United States Patent [19]

Murray et al.

[11] Patent Number: 5,001,233
[45] Date of Patent: Mar. 19, 1991

[54] SYNTHESIS OF HYDROXYLAMINES USING DIOXIRANES

[75] Inventors: Robert W. Murray, Creve Coeur; Megh Singh, St. Louis, both of Mo.

[73] Assignee: The Curators of the University of Missouri, Columbia, Mo.

[21] Appl. No.: 407,069

[22] Filed: Sep. 14, 1989

[51] Int. Cl.[5] .................. C07B 41/00; C07C 239/00; C07D 321/00; C07J 43/00

[52] U.S. Cl. ..................................... 540/29; 548/216; 548/565; 546/290; 564/300; 564/301

[58] Field of Search .................... 540/29; 564/300; 549/200; 548/565, 216; 546/290

[56] References Cited

PUBLICATIONS

Murray, Robert W. et al, "Dioxiranes: Synthesis and Reactions of Methyldioxiranes", *The Journal of Organic Chemistry* 50: 2847-2853 (1985).

Jean Jacques Yaouanc, et al, "Nucleophilic Oxidation with Bis Diphenylphosphinyl Peroxide: Direct Preparation of O-Phosphinylated Aminating Reagents", Synthesis 1985: 807 (Aug. 1985).

Murray, Robert W. et al, "A New Synthesis of Nitro Compounds Using Dimethyldioxirane", *Tetrahedron Letters* 27 (21): 2335-2336 (1986).

Murray, Robert W. and Singh, Megh, "A Convenient High Yield Synthesis of Nitroxides", *Tetrahedron Letters* 29 (37): 4677-4680 (Oct. 1988).

Zajec et al "Oxidation of Amines . . .", J. Am. Chem. Soc. 53 (25) 5856-5860 (1988).

*Primary Examiner*—Mark L. Berch
*Assistant Examiner*—Celia Chang
*Attorney, Agent, or Firm*—Haverstock, Garrett and Roberts

[57] ABSTRACT

The subject invention relates to a method of synthesizing hydroxylamines from secondary amines. This method uses a dioxirane compound such as dimethyldioxirane (DMD, which is relatively stable and simple to synthesize), as the oxidizing agent. The reaction proceeds as follows:

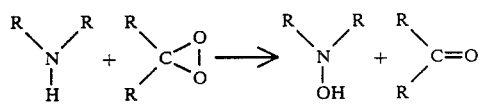

This method provides a simple, one-step reaction with high yields. It can be performed in acetone solution, and the transferral of an oxygen atom from dimethyldioxirane to the secondary amine converts the dioxirane into acetone, the solvent, permitting simple workup and purification. This method can be used with a wide variety of secondary amines, including aliphatic, aromatic, cyclic, and heterocyclic secondary amines, to create a corresponding variety of hydroxylamines.

4 Claims, 1 Drawing Sheet

Fig. 1

Fig. 1

SYNTHESIS OF HYDROXYLAMINES USING DIOXIRANES

GOVERNMENT SUPPORT

This invention was supported in part by a grant from the National Institutes of Health.

FIELD OF THE INVENTION

This invention is in the field of organic chemistry, and relates to the synthesis of hydroxylamines of secondary amines.

BACKGROUND OF THE INVENTION

Dioxirane compounds have the following structure:

Before it was isolated or proven to exist, Montgomery 1974 and Edwards 1979 (full citations are provided below) speculated that dimethyldioxirane (DMD) was present in certain reactions they were studying. DMD was first isolated by Robert W. Murray (one of the co-inventors of the subject invention) and his coworkers, and a method for synthesizing DMD in acetone solution is described in Murray et al 1985 (full citations are provided below). DMD can be synthesized in acetone solution at relatively low cost, and stored in a conventional freezer at about 0° C. for up to about a week with little or no degradation.

Various other dioxiranes have also been created, including methylethyldioxirane and diethyldioxirane (Murray 1985) and trifluoromethylmethyldioxirane (Mello et al 1988).

Dioxiranes are powerful oxidizing agents. For example, DMD has been used to oxidize primary amines, forming nitro compounds (Murray et al 1986). Eaton et al 1988 reported that dioxirane can be used to oxidize sensitive primary amines if the amine hydrochloride rather than the free amine is used. Zabrowski et al 1988 reports the use of dioxirane to oxidize substituted anilines to form nitro compounds. Prior to the subject invention, they had not been used to create hydroxylamines.

Hydroxylamines

Hydroxylamines derived from secondary amines are useful as intermediates in a variety of reactions. For example, they are used in the synthesis of nitrones which are used commercially as spin traps (Evans 1979), in the synthesis of nitroxides which are important as spin labels in probing biological structures (Berliner 1976 and Holtzman 1984), and as magnetic resonance imaging (MRI) contrast-enhancing agents (Keana et al 1985).

Some hydroxylamines also have direct utility. For example, heterocyclic hydroxylamines have various pharmacological and physiological activities. Some central nervous system depressants exhibit more activity in hydroxylamine form than in their amino or N-aryloxy derivatives (Klioze et al 1977). Sterically hindered hydroxylamines are used as bioantioxidants (Komoroy et al 1987), as inhibitors of lipid peroxidation (Zhdanoy et al 1988), and as suppressors of plant tumor growth (Serebryanyi et al 1985).

In the polymer industry, hydroxylamines are used as polymerization inhibitors for dienes (Japanese Patent JP 61,130,242; *Chem Abstr.* 105: 173217r, 1986) and for vinyl aromatic monomers (US patent 4,409,408, Miller). They are also used to stabilize polyolefins (Seltzer et al, APO appln. 138,767; *Chem Abstr.* 103: 72145u, 1985) and to prevent the premature oxidation of leuco dyes in photoimaging compounds (US patent 4,298,678, McKeever). Hydroxylamines have been used as catalysts in the facile hydration of nitriles to amides (Miyazawa et al 1964), and N,N-dialkyl hydroxylamines have been shown to be useful as precursors for synthesizing nitrenium ions (Gassman et al 1973).

Previous Methods of Synthesizing Hydroxylamines

Various methods have been reported for synthesizing hydroxylamines. For example, 2-(phenylsulfonyl)-3-aryloxaziridines (Davis et al 1986) can be used to synthesize hydroxylamines using secondary amine reagents (Zajac et al 1988). The hydroxylamines formed by that process are accompanied by varying amounts of nitrones. Gribble et al 1977 describes a general synthesis of hydroxylamines in which the corresponding oxime is reduced with sodium borohydride or lithium aluminum hydride. The oxidation of secondary amines with hydrogen peroxide gives hydroxylamines, but the yields are poor (Wolfenstein 1892; Henry et al 1950). Hydroxylamines are also available from the pyrolysis of tertiary amine oxides (Cope et al 1949; Rogers 1955).

Sterically hindered hydroxylamines are prepared via the reduction of corresponding nitroxides, using a variety of reducing agents (Paleos et al 1977; Rozantsey et al 1964 and 1966; Le Ⓡet al 1975; Dadonneau et al 1984). The drawback of such methods is that the nitroxides are often difficult to synthesize. Several groups have described the reduction of nitrones to hydroxylamines (Exner 1955; Hortmann et al 1978; Hammer et al 1964; Delpierre et al 1965).

The most common method of preparing hydroxylamines is the oxidation of a corresponding amine with benzoyl peroxide (Gambarajan 1925 and 1927; Biloski et al 1983). This method requires treatment of an intermediate 0-benzoylated hydroxylamine with base in order to obtain the free hydroxylamine. In a similar procedure developed by Sturtz and coworkers, an amine is oxidized with bis[diphenylphosphinyl]peroxide, creating an intermediate 0-diphenylphosphinyl-hydroxylamine, and the hydroxylamine is obtained by acidic hydrolysis of that intermediate (Yaouanc et al 1985). While that method generally gave good yields of hydroxylamines, it involved a two step process. In addition, Yaouanc et al 1985 reported that there was no generally reliable methodology for oxidizing secondary amines to form N,N-dialkylhydroxylamines.

Thus, the previously known methods of synthesizing hydroxylamines suffer from various limitations. Most previous methods of synthesis require multi-step reactions; they tend to suffer from low yields, and from unwanted by-products which may be very difficult yet necessary to remove before the desired hydroxylamines can be used for biological purposes. In addition, the prior methods of synthesizing hydroxylamines often require reagents that are expensive and/or difficult to synthesize.

The present invention, by contrast, provides a general method for synthesizing hydroxylamines from secondary amines. This method offers a simple, one-step process with very high yields and little or no unwanted by-products. It has been shown to work satisfactorily with different types of secondary amine reagents, including aliphatic, aromatic, cyclic, and heterocyclic secondary amines. With each type of reagent, the secondary amine group is attacked very selectively; therefore, there is no need to take special steps to protect and then deprotect other reactive groups.

SUMMARY OF THE INVENTION

The subject invention relates to a method of synthesizing hydroxylamines from secondary amines. This method uses a suitable dioxirane compound, such as dimethyldioxirane (DMD, which is relatively stable and simple to synthesize) as the oxidizing agent. The reaction proceeds as follows:

This method provides a simple, one-step reaction with high yields. It can be performed in acetone solution, and the transferral of an oxygen atom from the dioxirane to the secondary amine converts the dioxirane into acetone, the preferred solvent, permitting simple workup and purification. This method can be used with a wide variety of secondary amines, including aliphatic, aromatic, cyclic, and heterocyclic secondary amines, to create a corresponding variety of hydroxylamines.

DETAILED DESCRIPTION OF THE INVENTION

The subject invention involves the use of dioxirane compounds to convert secondary amines to their corresponding hydroxylamines.

The specific dioxirane compound used in the Examples is dimethyldioxirane (DMD). That particular derivative is used because (1) it is relatively simple and inexpensive to synthesize, (2) it is sufficiently stable for use in the subject invention, and (3) DMD yields a preferred solvent, acetone, rather than an undesired byproduct when it loses an oxygen atom. If desired, other dioxirane derivatives can be synthesized and used instead of dimethyldioxirane to convert secondary amines into hydroxylamines. Unless such other dioxirane derivatives are deliberately provided with highly reactive groups at other locations on the molecule, which might cause competing reactions, the dioxirane structure will react quickly and selectively with secondary amine groups to form hydroxylamines.

Table 1 summarizes the yields of several reactions described in the Examples. The compounds listed in Table 1 can serve as precursors for synthesizing nitroxides which have major commercial significance.

TABLE 1

| Yields of Hydroxylamines Which Can Serve As Precursors For Major Nitroxides | |
|---|---|
| Hydroxylamine | Yield (%) |
| 1,4-dihydroxy-2,2,6,6-tetramethyl piperidine | 99 |
| 4-hydroxy-3,3-dimethyl-1-oxa-4-azaspiro [4.5] decane | 96.2 |
| 4-hydroxy-3,3-dimethyl-1-oxa-4-azaspiro [4.6] undecane | 97 |
| 3'-hydroxy-4',4'-dimethylspiro-(5α-cholestane-3,2'-oxazolidine) | 97 |

TABLE 1-continued

| Yields of Hydroxylamines Which Can Serve As Precursors For Major Nitroxides | |
|---|---|
| Hydroxylamine | Yield (%) |
| 1-hydroxy-2,2,5,5-tetramethyl-pyrroline-3-carboxamide | |

The yield of 1-hydroxy-2,2,5,5-tetramethyl-pyrroline-3-carboxamide was not determined, because it is spontaneously oxidized by air. If desired, it can be created under a blanket of inert gas and in the absence of light, to avoid aerial oxidation.

Table 2 lists the yields of several other hydroxylamines which do not have large commercial markets at the present time. The subject invention, by providing a method of synthesizing those compounds at lower expense and higher yield, is likely to stimulate greater use of those compounds as well as other similar or related compounds.

TABLE 2

| Yields of Other Hydroxylamines | |
|---|---|
| Hydroxylamine | Yield (%) |
| N-hydroxy-N-tert-butyl benzylamine | 99.6 |
| N,N-dibenzylhydroxylamine | 98 |
| N-hydroxy-N-tert-butyl-N-p-nitrobenzylamine | 93 |
| N,N-diisobutylhydroxylamine | 97.4 |
| N,N-dicyclohexylhydroxylamine | 82.6 |

Table 3 lists hydroxylamines synthesized by the methods of this invention, which had never been previously reported to exist. To the best of the applicants' knowledge, this is the first time these compounds have ever been created.

TABLE 3

| Hydroxylamines Which Were Not Previously Reported | |
|---|---|
| 4-hydroxy-3,3-dimethyl-1-oxa-4-azaspiro [4.5] decane | 96.2 |
| 4-hydroxy-3,3-dimethyl-1-oxa-4-azaspiro [4.6] undecane | 97 |
| 3'-hydroxy-4',4'-dimethylspiro-(5α-cholestane-3,2'-oxazolidine | 97 |

Figure 1:
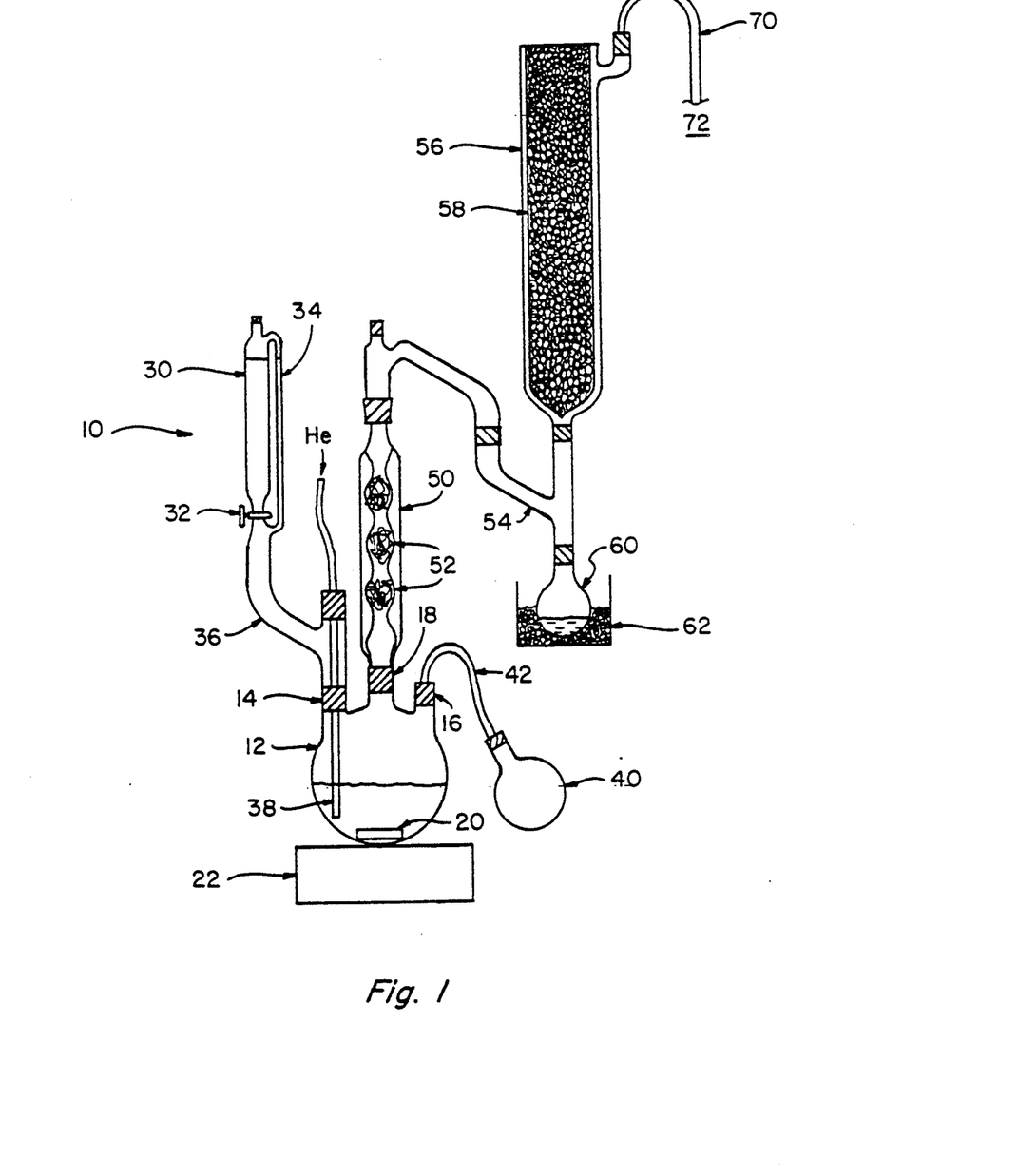

The equipment assembly 10 for creating the dimethyldioxirane used to carry out the method of this invention is shown in FIG. 1. The reaction vessel comprises a three-necked flask 12, wherein the three necks serve as inlets 14 and 16 and outlet 18. A magnetic stirring bar 20 is placed in the reaction vessel 12; it is rotated by a magnetic stirrer 22.

The reaction vessel 12 is initially charged with a mixture of acetone, water, and sodium bicarbonate. It is kept at room temperature during the DMD synthesis.

A liquid addition unit 30 with a stopcock 32 and a pressure equalizer 34 is coupled to inlet 14 of reaction vessel 12 via a Y-tube 36. A continuous supply of gaseous helium (an inert gas used as a carrier for the gaseous DMD) is provided to reaction vessel 12 via the other inlet provided by Y-tube 36. The helium is injected into the bottom region of reaction vessel 12 via tube 38. The inert carrier gas should be injected below the surface of the liquid, and can be dispersed throughout the reaction vessel by a dispersing nozzle or manifold on the bottom of the vessel.

Second inlet 16 of reaction vessel 12 is coupled to a vessel 40 which contains Oxone (a trademark of DuPont), a formulation containing monoperoxysulfuric acid, $2KHSO_5 \cdot KHSO_4 \cdot K_2SO_4$. The vessels are coupled via a device such as a flexible tube 42 which allows the Oxone (in granular form) to be added slowly to reaction vessel 12.

Outlet 18 of reaction vessel 12 is coupled to vapor column 50, which is packed with glass wool 52 to prevent any liquid from the reaction vessel 12 from spattering into the receiving flask. Vapors (which contain DMD and acetone) from the reaction vessel are carried through the glass wool 52 with the aid of the helium carrier gas. Those vapors enter Y-tube 54, which is connected to condensation unit 56. The interior chamber 58 of condensation unit 56 contains a very cold mixture such as dry ice and acetone. As the vapor which contains DMD contacts the cold surfaces in condensation unit 56, it condenses. The condensate collects in the main receiving flask 60, via Y-tube 54. The condensate chills the Y-tube 54 and the receiving flask 60, causing some of the vapors to condense directly into the receiving flask. The receiving flask is also chilled directly, by means such as dry ice-acetone bath 62.

Any vapors which are still in gaseous form after they pass through the condensation unit 56 can be collected via tube 70 in one or more cold traps 72 if desired. The applicants have found that a single trap containing dry ice and acetone is sufficient to collect the large majority of any remaining DMD. In industrial processes, it may be advisable to provide additional cold traps to ensure complete removal of any DMD.

The DMD/acetone mixture collected in receiving flask 60 and in any cold traps can be stored in a conventional freezer (at 0° C. or slightly colder temperatures) for up to about seven days with little or no degradation. If storage for more than a few days is required, the concentration of the DMD should be assayed shortly before it is used.

The concentration of DMD in acetone solution can be assayed by various methods, In the work described in the Examples, the DMD concentrations were determined by the phenyl methyl sulfide method (Murray et al 1985). Other methods include a triphenylphosphine method (Murray et al 1985), UV spectroscopy (absorbance at 331–335 nm), and iodometric titration.

Reaction of an exactly balanced stoichiometric amount of dioxirane with a selected secondary amine leads, after solvent removal, to the solid hydroxylamine. In most cases, the oxidation reaction is highly selective. For example, 1,4-dihydroxy-2,2,6,6-tetramethyl piperidine was prepared in high yield with no oxidation of the secondary alcohol group. In some cases, dioxirane oxidizes secondary alcohols to the corresponding ketone (Murray et al 1986). Apparently, the rate difference is heavily in favor of amine oxidation in the piperidine reaction. The same is believed likely to apply with regard to other compounds having both secondary amine and secondary alcohol groups.

After the conversion of a secondary amine to a hydroxylamine is completed, using equimolar quantities of DMD and a secondary amine, the resulting hydroxylamine can be converted into a nitroxide or nitrone via a second reaction if an additional quantity of DMD is added. In most cases, the DMD reaction highly favors the secondary amine group rather than the hydroxylamine group. This normally leads to high yields of relatively pure hydroxylamines, as indicated in Tables 1 and 2, with little or no nitroxide present. However, when certain types of secondary amines are reacted with equimolar DMD, competing reactions can form small but significant quantities of nitroxides and/or nitrones. For example, N-phenyl-N-benzylamine is oxidized to a reaction mixture containing a majority of the hydroxylamine mixed with smaller quantities of nitroxides, nitrones, and unreacted amine. Such mixtures can be purified, if the hydroxylamine is the desired product.

It should also be noted that the oxidation reactions described in the Examples have been performed on a variety of secondary amine compounds which have relatively reactive groups that were not altered by the dimethyldioxirane. Example 1 shows that a secondary alcohol group was left undisturbed by DMD oxidation. Example 2 shows that an aromatic ring was not altered or substituted. Examples 3 and 4 show that bicyclic groups with spiro configurations (i.e., the adjoining rings share a single carbon atom) were undisturbed, and that heterocyclic rings containing oxygen atoms were undisturbed. Example 5 shows that a complex polycyclic molecule (which functions as a precursor to several important cholesterol derivatives) was unaltered. Example 7 shows that (1) an unsaturated ring having a double bond was undisturbed, and (2) a relatively reactive carboxamide group was undisturbed. Example 8 shows that a nitro group was not disturbed.

In addition, Murray et al 1988 indicates that several types of nitroxides were synthesized by reacting secondary amines with 2× molar quantities of DMD. Since those nitroxides were formed in a set of two reactions (i.e., conversion of the amine into a hydroxylamine, and conversion of the hydroxylamine into the nitroxide, all in a single vessel), it is clear that the potentially competing reactive groups contained on the secondary amines mentioned in that paper were also undisturbed by the DMD oxidation reaction. Those potentially reactive groups included a carboxylic acid group, a ketone, an oxime, an unsaturated ring with double-bonded carbons, and a group with triple-bonded carbons.

Thus, this reaction has been shown to be highly selective for secondary amine groups, despite the presence of various types of potentially competing reactive groups.

EXAMPLES

Reagents

Acetone (Fisher Chemicals, Fair Lawn NJ), was fractionally distilled over anhydrous potassium carbonate. Benzene (Fisher), toluene (Fisher), petroleum ether (Fisher), diethyl ether (Fisher), and ligroin (MCB, Norwood OH) were purified by distillation before use. 5-δ-cholestane-3-one and 2-amino-2-methyl-1-propanol were obtained from Aldrich (Milwaukee, WI) and were of highest commercial purity. N-tert-butyl-N-benzylamine (Aldrich), N,N-dibenzylamine (Aldrich), N,N-diisobutylamine (Aldrich), N,N-dicyclohexylamine (Kodak, Rochester NY) were fractionally distilled under reduced pressure before use. Oxone (DuPont), $2KHSO_5 \cdot KHSO_4 \cdot K_2SO_4$ was obtained from Aldrich and used without further purification. Anhydrous $K_2CO_3$ (Aldrich), anhydrous sodium sulfate (Aldrich), sodium borohydride (Ventron, Beverly MA) and anhydrous magnesium sulfate (Fisher) were used as such.

All boiling points (bp), melting points (mp), and other temperatures are expressed in degrees Celsius. Unless otherwise specified, "cold" solutions were kept in ice baths at approximately 0° C. All stirring was done using magnetic stirring bars (although mechanical stirring could be used if desired), and all mixing of solutions was done dropwise.

Synthesis and Storage of DMD

Acetone solutions containing dimethyldioxirane (DMD) were prepared by the method of Murray et al 1985, scaled up as follows and using only one cold trap instead of five. A 2000 ml 3-necked round bottom flask containing a mixture of water (80 ml), acetone (50 ml, 0.68 mol) NaHCO₃ (96 g), and a stirring bar was coupled via a rubber tube to a flask containing granular Oxone (180 g, 0.29 mol). A pressure-equalized dropping funnel containing water (60 ml) and acetone (60 ml, 0.82 mol) was coupled to another neck of the flask, via a Y-tube as shown in FIG. 1. A vapor column, loosely packed with glass wool, was attached to the third neck of the reaction vessel.

The outlet of the air condenser was connected to an acetone-dry ice condenser, which was attached to a receiving flask (100 ml) cooled in an acetone-dry ice bath. The receiving flask was connected to a dry ice-acetone cold trap.

Helium was bubbled through the reaction mixture while the granular Oxone was added in small portions by lifting the Oxone flask. The acetone-water mixture was added simultaneously, dropwise. The mixture was stirred vigorously at room temperature throughout the reaction period. After 15 min of reaction time, a slight vacuum was applied to the reaction assembly using a water aspirator.

The yellow-colored DMD-acetone solution collected primarily in the receiving flask; some material was found in the cold trap. The two solutions were mixed, stirred briefly with sodium sulfate to remove part of the water, filtered, and stored at 0 to −5° for up to about seven days.

Solutions were assayed for DMD content using phenyl methyl sulfide. The concentrations were in the range of 0.04 to 0.185 M. Quantities of solution added to secondary amine reagents were varied accordingly, to achieve exactly 1:1 molar ratios.

Analytical Instrumentation $^1$H and $^{13}$C NMR data were obtained in CDCl₃ solution at 300 MHz and 75 MHz, respectively, on a Varian XL-300 fourier transform spectrometer. $^1$H NMR spectra used the 7.24 ppm resonance of residual chloroform as an internal standard; $^{13}$C NMR spectra used the CDCl₃ resonance at 77.00 ppm as an internal standard. In both $^1$H NMR and $^{13}$C NMR chemical shifts are reported in δ units downfield from tetramethylsilane. Infrared spectra were recorded on a Perkin-Elmer model 783 grating spectrophotometer in KBr pellets. Mass spectra were recorded on either a Finnigan 4500 twin EI and CI quadrupole mass spectrometer or on an Associated Electronics Industries model MS-1201B mass spectrometer at 70 eV unless otherwise noted, with pertinent peaks reported as m/e (relative intensity). GC-Mass spectra were recorded on either a Hewlett-Packard 5992 model gas chromatograph-mass spectrometer (DB-5 Megabore column), where the peak finder program was used for product analysis and the SIM (selected ion monitoring) program was used for obtaining ion ratios, or on a Hewlett-Packard 5988A twin EI and CI quadrupole mass spectrometer at 70 eV by a direct probe. GC-Mass spectra were recorded on the HP 5988A model instrument using a gas chromatograph (HP-1 column, 15 meters). Melting points were measured on either a Dynamics optics AHT 713921 hot-stage apparatus or on a Thomas-Hoover capillary melting point apparatus and are uncorrected. Elemental analyses were performed by Atlantic Microlab, Inc. (Atlanta, GA).

EXAMPLE 1

Preparation of 1,4-dihydroxy-2,2,6,6-tetramethyl-piperidine 2,2,6,6-tetramethyl-4-piperidinol was prepared by the reduction of 2,2,6,6-tetramethyl-4-piperidone (Aldrich) with sodium borohydride. It was purified by recrystallization from ligroin (bp 65–90). It formed colorless needles with mp 130–131; the reported mp is 128–131 (Lutz et al 1962).

In a 100 ml flask, a solution of 0.047 M DMD in acetone (21.2 ml, 1 mmol) was added to a cold stirred solution of 2,2,6,6-tetramethyl-4-piperidinol (0.1572 g, 1 mmol) in acetone (10 ml). The reaction mixture was stirred for two hours in an ice bath. Solvent was removed on a rotary evaporator to give a white crystalline solid (0.1727 g, 99% yield, mp 161–163). Sublimation on the Kugelrohr (110–120°, 1×10⁻⁴ mmHg) gave white needles (0.170 g). Measured mp was 162–163; reported mp is 155–159 (Lee et al 1975 and Rozantsey et al 1966).

The secondary amine and the hydroxylamine have the following structures:

IR (KBr, cm⁻¹): 3410 (OH), 3520 (N—OH), 1378 and 1365 (gem-dimethyl).

$^1$H NMR: δ1.15 (s, 6 H), 1.19 (s, 6 H), 1.44 (t, 2 H, J=12 Hz), 1.88 (dd, 2 H, J=12.2, 3.5 Hz), 3.88 (m, 1 H).

$^{13}$C NMR: δ20.07, 32.30, 48.02, 8.97, and 63.22.

EXAMPLE 2

Preparation of N-hydroxy-N-tert-butylbenzylamine

A solution of 0.057 M DMD in acetone (47.4 ml, 2.7 mmol) was added to a cold stirred solution of N-tert-butyl-N-benzylamine (Aldrich, 0.4417 g, 2.7 mmol) in acetone (5 ml). The reaction mixture was stirred for fifteen minutes in an ice bath. Solvent was removed on a rotary evaporator to give a white, microcrystalline solid (0.4803 g, 99.6% yield), mp 58–60. Flash chromatography of the solid over silica gel and elution with a 90:10 mixture of petroleum ether (bp 35–60) and ethyl acetate gave the hydroxylamine as a white crystalline solid, mp 60–61.5 (reported mp 71–73, Emmons 1957). Distillation of this material gave a solid with the same mp.

The hydroxylamine has the following structure:

IR (KBr, cm⁻¹): 3340 (N—OH), 1460, 1365 (tert-butyl)

$^1$H NMR: δ1.19 (s, 9 H), 3.75 (s, 2 H), 4.42 (s, br, 1 H, N—OH, exchangeable with D$_2$O), 7.20–7.40 (m, 5 H)

$^{13}$C NMR: δ25.41, 56.34, 58.75, 126.83, 128.18, 129.21, 139.70

Mass (EI, 70 eV): 179 (M+, 3.5).

EXAMPLE 3

Preparation of 4-hydroxy-3.3-dimethyl-1-oxa-4-azasoiro[4.5]decane

Oxazolidines were synthesized by the procedures of Hancock 1944 and Keana 1967, and were purified by fractional distillation under reduced pressure. The 3,3-dimethyl-1-oxa-4-azaspiro[4.5]decane had a measured bp 98-99 at 20 mmHg: the reported bp was 95-97.5 at 20 mmHg (Hancock 1944)

A solution of 0.047 M DMD in acetone (45.1 ml, 2.12 mmol) was added to a cold stirred solution of 3,3-dimethyl-1-oxa-4-azaspiro[4.5]decane (0.3592 g, 2.12 mmol) in acetone (5ml). The reaction mixture was stirred for two hours in the ice bath. Evaporation of the solvent from the colorless solution on the rotary evaporator gave a white crystalline solid which was dried in vacuo for two hours. The yield was 0.378 g (96.2%). Sublimation of the solid on the Kugelrohr apparatus (110–115°, 0.2 mmHg) gave a White crystalline solid, mp 133–135.

This hydroxylamine, which has not been previously reported, has the following structure:

IR (KBr, cm$^{-1}$): 3300 (N—OH), 1380 and 1365 (gem-dimethyl), and 1060 (C-0-C).

$^1$H NMR: δ1.24 (s, 6 H), 1.44–81 (m, 10 H), 3.59 (s, 2 H), and 7.17 (br, s, 1 H)

$^3$C NMR: δ23.15, 23.57, 25.22, 34.23, 63.92, 73.52, 99.28.

Elemental analysis, calculated for C$_{10}$H$_{19}$NO$_2$ C, 64.82; H, 10.33; N, 7.55. Measured: C, 65.02; H, 10.35; N, 7.49.

EXAMPLE 4

Preparation of 4-Hydroxy-3.3-dimethyl-1-oxa-4-azasoiro[4.6]-undecane 3,3-Dimethyl-1-oxa-4-aza spiro[4.6]undecane was synthesized by the method of Chou et al 1974. The measured bp was 135 at 28 mmHg; reported bp 122-123 at 19 mmHg.

A solution of 0.44 M DMD in acetone (26.2 ml, 1.16 mmol) was added to a cold stirred solution of 3,3- di-methyl-1-oxa-4-azaspiro[4.6]undecane (0.2127 g, 1.16 mmol) in acetone (5 ml). The mixture was stirred for two hours in the ice bath. The solvent was evaporated to give a white crystalline solid (0.224 g, 97% yield), mp 94-95°. A portion of the product was sublimated (70-80°, 0.2 mmHg) to give an analytical sample as white needles, mp 97-99.

This hydroxylamine, which has not been previously reported, has the following structure:

IR (KBr, cm$^{-1}$): 3250 (N—OH), 1385 and 1370 (gem-dimethyl), 1075 (C-0-C).

$^1$H NMR: δ1.22 (s, 6 H), 1.40-2.20 (m, 12 H), 3.55 (s, 2 H), and 6.80 (br, s, 1 H).

$^{13}$C NMR: δ22.89, 23.06, 30.01, 37.87, 63.30, 73.36, and 102.45.

Elemental analysis, calculated for C$_{11}$H$_{21}$NO$_2$: C, 66.30; H, 10.62; N, 7.02. Measured: C, 66.23; H, 10.67; N, 7.06.

EXAMPLE 5

Preparation of 3′-hydroxy-4′4′-dimethylsoiro-[5δ-cholestane-3,2′-oxazolidinel 4,4′-Dimethylspiro[5-δ-cholestane-3,2′-oxazolidine]- was prepared by the method of Keana et al 1967. A solution of 5 δ- cholestan-3-one (1.53 g, 3.95 mmol), 2-amino-2-methyl-1-propanol (1 ml, excess 10.47 mmol), dry toluene (60 ml), and p-toluene sulfonic acid monohydrate (0.050 g) was refluxed for 60 hours with continuous water removal by means of a Dean-Strak trap. Toluene was washed with 100 ml of a saturated NaHCO$_3$ brine solution (4×50 ml) and water (4×50 ml). The washed toluene layer was dried with anhydrous Na$_2$SO$_4$. The toluene was removed on a rotary evaporator to give a white microcrystalline solid (1.8 g). The measured mp was 120–125; the reported mp was 124–125 (Keana et al 1967).

A solution of 0.051 M DMD in acetone (9.8 ml, 0.5 mmol) was added to a cold solution of 4′,4′-dimethyl-spiro[5 δ-cholestane -3,2′-oxazolidine](0.2289 g, 0.5 mmol) in acetone (25 ml). A white precipitate immediately began separating out. Stirring was continued for two hours in an ice bath. Solvent was removed on the rotary evaporator to give a white microcrystalline solid (0.236 g, 99%), mp 178–181. The solid was suspended in degassed methanol (30 ml) and filtered in vacuo. The solid was washed with degassed methanol (2×10 ml) and dried on a vacuum line for three hours to give a white microcrystalline solid (0.230 g, 97%), mp 180–183.

This hydroxylamine, which has not been previously reported, has a specific utility. It can serve as a precursor for synthesizing a nitroxide compound which is used as a "spin label" during various types of medical and biochemical procedures. The hydroxylamine has the following structure:

IR (KBr, cm$^{-1}$): 3250 (N—OH), 2980, 2940, 2870, 1465, 1455, 1440, 1382, and 1365(gem-dimethyl), 1300, 1285, 1260, 1175, 1135, 1105, 1090, 1068 (C-O-C), 995, 932, 810.

$^1$H NMR: $\delta$1.22 (4',4'—CH$_3$), 3.60 (5'—CH$_2$—), 5.90 (br, s, N-OH).

$^{13}$C NMR: $\delta$99.30 (C—3,2' spiro), 73.49 (C—5'—CH$_2$—, oxazolidine), 63.20 (C-4'), 56.12, 55.80, 53.70, 42.24, 39.67, 39.14, 36.38, 35.79, 35.41, 35.10, 35.01, 34.88, 31.58, 29.68, 28.32, 27.87, 27.64, 23.83, 23.65, 23.42, 23.29, 22.46, 22.19, 20.72, 18.29, 11.74, 11.26.

Elemental analysis, calculated for C$_{31}$H$_{53}$NO$_2$: C, 78.48; H, 11.70; N, 2.95. Measured: C, 77.99; H, 11.55; N, 2.92.

EXAMPLE 6

Preparation of N,N-dibenzylhydroxylamine

A solution of 0.051 M dimethyldioxirane in acetone (32.9 ml, 1.67 mmol) was added to a cold stirred solution of N,N-dibenzylamine (Aldrich; 0.331 g, 1.67 mmol) in acetone (5 ml). The mixture was stirred for fifteen minutes in an ice bath. Evaporation of the solvent on the rotary evaporator gave a white crystalline solid. The solid was dissolved in acetone and the solution dried with anhydrous Na$_2$SO$_4$. The solvent was removed to give a chromatographically homogeneous white solid (0.352 g, 98% yield). Measured mp was 121–122; reported mp is 122–123 (DeLaMare et al 1963).

The hydroxylamine has the following structure:

IR (KBr, cm$^{-1}$): 3320 (br, N-OH), 1495, 1455, 1385, 1342, 1075, 1030, 1020, 985, 940, 920, 845, 820, 760, 755, 700, 620, 520.

$^1$H NMR: $\delta$3.85 (s, 4 H, —CH$_2$—), 5.52 (br, s, 1 H, N—OH), 7.35 (m, 10 H, C$_6$H$_5$—).

$^{13}$C NMR: $\delta$63.75 (—CH$_2$—), 127.4 (C-4), 128.26 (C-3), 129.7 (C-2), 137.18 (C-1, >C—CH$_2$—N—).

EXAMPLE 7

Preparation of 1-hydroxy-2,2,5,5-tetramethyl-pyrroline-3-carboxamide

A solution of 0.066 M DMD in acetone (9 ml, 0.59 mmol) was added to a cold stirred solution of 2,2,5,5-tetramethyl-pyrroline-3-carboxamide (Frinton, Vineland NJ, 100 mg, 0.59 mmol) in acetone (5 ml). The mixture was stirred for two hours. Evaporation of the solvent on a rotary evaporator gave a colorless crystalline solid which was dried in vacuo for 6 hours. Sublimation of the solid at 10$^{-3}$ torr gave a white solid, mp 65-171.

The hydroxylamine has the following structure:

$^1$H NMR: $\delta$6.11 (s, 1 H), 5.48 (br, s, 2 H), 4.60 (br, s, 1 H), 1.25 (s, 6 H), 1.39 (s, 6 H).

Mass Spectrum, measured, 184 (M+); calculated, 184.23.

EXAMPLE 8

Preparation of N-hydroxy-N-tert-butyl-N-onitrobenzylamine

N-t-butyl-N-p-nitrobenzylamine was prepared by sodium borohydride reduction of the corresponding imine in methanol (Billman et al 1957). A solution of 0.056 M DMD in acetone (50.5 ml, 2.80 mmol) was added to a cold stirred solution of N-(t-butyl)-N-p-nitrobenzylamine (0.5844 g, 2.80 mmol) in acetone (5 ml). The reaction mixture was stirred for ten minutes in an ice bath. Solvent was removed on a rotary evaporator to give a pale yellow viscous liquid which crystallized to a pale yellow crystalline solid (0.6398 g). The solid was purified by passing it through a bed of silica gel (12 g) and eluting with ethyl acetate petroleum ether (10:90). Evaporation of the solvent gave a very pale yellow liquid which crystallized to a very pale yellow crystalline solid (0.585 g, 93% yield), mp 70-72.

The hydroxylamine has the following structure:

IR (KBr, cm$^-$): 3530 (N—OH), 2975, 2890, 1605, 1515, 1460, 1390, 1355, 1340, 1325, 1230, 1205, 1110, 1080, 1015, 994, 918, 860, 812, 735, 692, 540, 530.

$^1$H NMR: $\delta$1.21 (s, 9 H, —C(CH$_3$)$_3$), 3.86 (s, 2 H, —CH$_2$—N—)4.36 (s, 1 H, N-OH, exchangeable with D$_2$O), 7.54 (d, 2 H, J=8.75 Hz, aromatic), 8.18 (d, 2 H, J=8 75 Hz, aromatic).

$^{13}$C NMR: $\delta$25.32 (C(CH$_3$)$_3$), 55.71 (—C(CH$_3$)$_3$), 59.10 (—CH$_2$—N—), 123.41, 129.65, 146.98, 147.62.

Mass Spec (EI, 70 eV): 224 (M+), 57 (100, base peak).

EXAMPLE 9

Preparation of N,N-dicyclohexylhydroxylamine

A solution of 0.057 M DMD in acetone (49.2 ml, 3.317 mmol) was added to a cold stirred solution of N,N-dicyclohexylamine (Kodak; 0.508 g, 3.317 mmol) in acetone (5 ml). The reaction mixture was stirred for ten minutes in an ice bath. The solution was dried over Na$_2$SO$_4$, filtered, and the solvent removed in vacuo to give a colorless crystalline solid. This solid was purified by flash chromatography on silica gel with ethyl acetate:petroleum ether (20:80) elution to give a white crystalline solid (0.457 g, 82.6% yield), mp 70-72.

The hydroxylamine has the following structure:

IR (KBr, cm$^{-1}$): 3390, 3120, 2930, 2830, 1465, 1452, 1440, 1410, 1385, 1365, 1335, 1300, 1260, 1185, 1105, 955, 895, 850.

$^1$H NMR: $\delta$1.13 (m, 20 H, —CH$_2$—) 2.70 (m, methine H), 4.38 (br, s, 1 H, N-OH, exchangeable with D$_2$O)

$^{13}$C NMR: $\delta$25.20, 25.92, 28.66, 60.14.

Mass Spec (EI): 198.35 (M+1, 3), 197.35 (M+, 24).

EXAMPLE 10

Preparation of N.N-diisobutylhydroxylamine

A solution of 0.057 M DMD in acetone (52.1 ml, 2.96 mmol) was added to a cold stirred solution of N,N-diisobutylamine (Aldrich; 0.383 g, 2.96 mmol) in acetone (5 ml). The mixture was stirred for ten minutes in an ice bath. The acetone was distilled off and the residue dissolved in petroleum ether and the solution dried with $Na_2SO_4$. The hydrochloride salt was prepared by passing HCl gas into a solution of the hydroxylamine, which was chromatographically homogeneous, in petroleum ether. The white solid which formed was filtered off, washed with petroleum ether and dried in vacuo. The white crystalline solid obtained (0.525 g, 97.5% yield) had mp 133-136. The free hydroxylamine crystallized from aqueous ethanol had mp 55-57; reported mp 57-58 (Cope et al 1957). The hydroxylamine has the following structure:

IR (KBr, $cm^{-1}$): 3260 (N—OH), 2970, 2880, 2840, 1470, 1440, 1388, 1370, 1305, 1180, 1120, 1085, 1000, 955, 930, 904, 820, 750, 505, 520.

$^1$H NMR: δ0.92 (d, 12 H, J=6.6 Hz, CH3), 1.87 (m, 2 H, =CH-), 2.23 (d , 4 H, J=7Hz, -CH2-), 4.77 (br, s, 1 H, -OH).

$^{13}$C NMR: δ20.76 (CH3), 26.24 (=CH-), 69.04 (-CH2-).

REFERENCES

Berliner, J. L., Ed., *Spin Labellino, Theory and Applications*, Academic Press, New York, 1976.
Billman, J.H. et al, *J. Org. Chem.* 22: 1068, 1957.
Biloski, A. J., et al, *Synthesis* 1983: 537, 1983
Chou, S., et al, *J. Org. Chem.* 39: 2356, 1974
Cope, A. C., et al, *J. Am. Chem. Soc.* 71: 3929, 1949
Cope, A. C., et al, *J. Am. Chem. Soc.* 79: 964, 1957
Dadonneau, M., et al, *Synthesis* 1984: 895, 1984
Davis, F. A., et al, *J. Org. Chem.* 51: 4240, 1986
DeLaMare, H. E., et al, *J Org. Chem.* 28: 1068, 1963
Delpierre, G R., et al, *Quart. Rev. Chem. Soc.* 19: 329, 1965
Eaton, P.E., et al, *J. Org. Chem.* 53: 5353, 1988
Emmons, W. D., *J. Am. Chem. Soc.* 79: 5739, 1957
Evans, C. A., *Aldrichimica Acta* 12: 23, and references cited therein, 1979
Exner, O., *Coll Czech. Chem. Comm.* 20: 202, 1955
Gambarajan, S., *Ber. Dtsch. Chem. Ges.* 58: 1775, 1925
Gambarajan, S., et al, *Ber. Dtsch. Chem. Ges* 60: 390, 1927
Gassman, P. G., et al, *J. Am. Chem. Soc.* 95: 449, 1973
Gribble, G. W., et al, *Synthesis* 1977: 856, 1977
Hammer, J., et al, *Chem. Rev.* 64: 473, 1964
Hancock, E. M., et al, *J. Am. Chem. Soc.* 66: 1738, 1944
Henry, R. A., et al, *J. Am. Chem. Soc.* 72: 2280, 1950
Holtzman, J. L., Ed., *Spin Labellino in Pharmacology*, Academic Press, N.Y., 1984.
Hortmann, A. G., et al, *J. Org. Chem.* 43: 2289, 1978
Japanese Patent, Kokai Tokyo Koho, JP 61,130,242 [86,130,242], Atlantic Richfield Co., *Chem. Abstr.* 105: 173217r, 1986
Keana, J. F. W , et al, *Physiolog. Chem. Phys. Med. NMR* 17: 235, 1985
Keana, J. F. W., et al, *J. Am. Chem. Soc.* 89: 3055, 1967
Klioze, S. S., et al, *J. Med. Chem.* 20: 610, 1977
Komoroy, P. G., et al, *Dokl. Akad. Nauk. SSSR* 297: 734, 1987
Lee, T. B., et al, *J. Org. Chem.* 40: 3145, 1975
Lutz, W. B., et al, *J. Org. Chem.* 27: 1695, 1962
Mello, R., et al, *J. Org. Chem.* 53: 3890, 1988
Miyazawa, T., et al, *Synthesis* 1964: 1034, 1964
Murray, R. W., et al, *J. Org. Chem.* 50: 2847, 1985
Murray, R. W., et al, *Tetrahedron Lett.* 27: 2335, 1986
Murray, R. W., et al, *Tetrahedron Lett.* 29: 4677, 1988
Paleos, C. M., et al, *J. Chem. Soc., Chem. Comm.* 1977: 345, 1977
Rogers, M.A.T., *J. Chem. Soc.* 1955: 769, 1955
Rozantsey, E. G., et al, *Izy. Akad. Nauk., SSSR, Ser. Khim.* 1123, 1964
Rozantsey, E. G., et al, *Izy. Akad. Nauk. SSSR, Ser. Khim* 891, 1966
Seltzer, R., et al, Eur. Patent Appl , 138,767, *Chem. Abstr.* 103: 72145u, 1985
Serebryanyi, A. M., et al, *Izy. Akad. Nauk. SSSR, Ser. Biol.* 1985: 767, 1985
Wolfenstein, R., *Ber. Dtsch. Chem. Ges.* 25: 2777, 1892
Yaouanc, J. J., et al, *Synthesis* 1985: 807, 1985
Zabrowski, D. L., et al, *Tetrahedron Lett.* 29: 4501, 1988
Zajac, W. W., et al, *J. Org. Chem.* 53: 5856, 1988
Zhdanov, R. I., et al, *Khim.-Farm. Zh.* 22:, 147, 1988

We claim:

1. A method of synthesizing a hydroxylamine of a secondary amine, comprising the step of reacting a secondary amine with a dioxirane compound.

2. A method of Claim 1, wherein the dioxirane compound comprises dimethyldioxirane.

3. A method of Claim 1, wherein the reaction is carried out in acetone solution.

4. A method of Claim 2, wherein the reaction is carried out in acetone solution.

* * * * *

UNITED STATES PATENT AND TRADEMARK OFFICE
CERTIFICATE OF CORRECTION

PATENT NO. : 5,001,233

DATED : March 19, 1991

INVENTOR(S) : Robert W. Murray and Megh Singh

It is certified that error appears in the above-identified patent and that said Letters Patent is hereby corrected as shown below:

Column 2, line 1, "Zhdanoy" should be --Zhdanov--.

Column 2, line 35, "Le®" should be --Lee--.

Column 4, line 66, "$2KHSO_5 \cdot KHSO_4 \cdot K_2SO_04$" should be "$2KHSO_5 \cdot KHSO_4 \cdot K_2SO_4$"

Column 8, line 42, "8.97" should be --58.97--.

Column 9, line 5 "(M+,3.5)" should be --$(M^+,3.5)$--.

Column 9, line 9, "azasoiro" should be --azaspiro--.

Column 9, line 21, "(5ml)" should be --(5 ml)--.

Column 9, line 27, "White" should be --white--.

Column 9, line 42, "3C NMR:" should be --$^{13}$C NMR:--.

Column 9, line 51, "3.3" should be --3,3-- and "azasoiro" should be --azaspiro--.

Column 10, line 21, "dimethylsoiro" should be --dimethylspiro--.

Column 10, line 22, "oxazolidinel" should be --oxazolidine]--.

Column 11, line 17, "N.N" should be --N,N--.

UNITED STATES PATENT AND TRADEMARK OFFICE
CERTIFICATE OF CORRECTION

PATENT NO. : 5,001,233

DATED : March 19, 1991

INVENTOR(S) : Robert W. Murray and Megh Singh

It is certified that error appears in the above-identified patent and that said Letters Patent is hereby corrected as shown below:

Column 11, line 48, "2.2" should be --2,2--.

Column 12, line 1, "(M+) should be --($M^+$)--.

Column 12, line 6, "-onitrobenzylamine" should be --p-nitrobenzylamine--.

Column 12, line 19, "acetate petroleum" should be --acetate:petroleum--.

Column 12, line 30, "(KBr,cm$^-$):" should be --(KBr,cm$^{-1}$):--.

Column 12, line 32, "8I2" should be --812--.

Column 12, line 39, "(M+) should be --($M^+$)--.

Column 13, line 1, "(M+,24) should be --($M^+$,24).

Column 13, line 4, "N.N" should be --N,N--.

Column 13, line 31, "CH3" should be --$CH_3$--.

Col. 13, line 32, "-CH2-)" should be ---$CH_2$-)--.

Column 13, line 38, "Labellino" should be --Labelling--.

Column 13, line 48, "G R." should be --G.R.--.

UNITED STATES PATENT AND TRADEMARK OFFICE
CERTIFICATE OF CORRECTION

PATENT NO. : 5,001,233

DATED : March 19, 1991

INVENTOR(S) : Robert W. Murray and Megh Singh

It is certified that error appears in the above-identified patent and that said Letters Patent is hereby corrected as shown below:

Column 14, line 9, "Labellino" should be --Labelling--.

Column 14, line 31, "Rozantsey" should be --Rozantsev-- and "Izy." should be --Izv.--.

Column 14, line 32, insert --1964-- after "Khim."

Column 14, line 33, "Rozantsey" should be --Rozantsev-- and "Izy." should be --Izv.--.

Col. 14, lines 32 and 34 insert --1964-- and -- 1966-- after "Khim."

Column 14, line 37, "Izy." should be --Izv.--.

Column 14, line 39, "I892" should be --1892--.

Signed and Sealed this

Nineteenth Day of January, 1993

*Attest:*

DOUGLAS B. COMER

*Attesting Officer*     *Acting Commissioner of Patents and Trademarks*